United States Patent [19]

Pall et al.

[11] Patent Number: 5,360,545
[45] Date of Patent: Nov. 1, 1994

[54] FILTER FOR OBTAINING PLATELETS

[75] Inventors: David B. Pall, Roslyn Estates; Thomas C. Gsell, Glen Cove, both of N.Y.

[73] Assignee: Pall Corporation, Glen Cove, N.Y.

[21] Appl. No.: 100,919

[22] Filed: Aug. 3, 1993

Related U.S. Application Data

[60] Division of Ser. No. 846,587, Mar. 5, 1992, Pat. No. 5,258,126, which is a continuation-in-part of Ser. No. 609,574, Nov. 6, 1990, Pat. No. 5,152,905, which is a continuation-in-part of Ser. No. 405,977, Sep. 12, 1989, abandoned, and a continuation-in-part of Ser. No. 609,654, Nov. 6, 1990, Pat. No. 5,100,564.

[51] Int. Cl.$^5$ .................... B01D 39/00; B01D 39/16
[52] U.S. Cl. .................... 210/505; 210/435; 210/491; 210/508
[58] Field of Search ............ 210/435, 489, 446, 491, 210/506, 507, 508, 503, 504, 505; 422/101; 604/4, 5, 406, 410

[56] References Cited

U.S. PATENT DOCUMENTS

| | | | |
|---|---|---|---|
| 2,834,730 | 5/1958 | Painter, Jr. et al. | 210/504 |
| 2,956,899 | 10/1960 | Cline | 522/144 |
| 3,111,424 | 11/1963 | LeClair | 522/144 |
| 3,268,622 | 8/1966 | Stanton et al. | 522/144 |
| 3,274,294 | 9/1966 | Stanton et al. | 522/144 |
| 3,448,041 | 6/1969 | Swank | 210/446 |
| 3,513,976 | 5/1970 | James | 210/782 |
| 3,565,780 | 2/1971 | Zimmerman | 522/144 |
| 3,593,854 | 7/1971 | Swank | 210/436 |
| 3,663,374 | 5/1972 | Moyer et al. | |
| 3,765,536 | 10/1973 | Rosenberg | 210/446 |
| 3,877,978 | 4/1975 | Kremen et al. | 210/508 |
| 3,905,905 | 9/1975 | O'Leary et al. | 210/436 |
| 3,935,110 | 1/1976 | Schmid et al. | 210/456 |
| 3,935,111 | 1/1976 | Bentley | 210/446 |
| 3,954,621 | 5/1976 | Etani et al. | 210/416 |
| 4,009,714 | 3/1977 | Hammer | 210/436 |
| 4,009,715 | 3/1977 | Forberg et al. | 210/455 |
| 4,040,959 | 8/1977 | Berman et al. | 210/782 |
| 4,073,732 | 2/1978 | Lauer et al. | 210/491 |
| 4,081,402 | 3/1978 | Levy et al. | 424/78 |
| 4,087,363 | 5/1978 | Rosemeyer et al. | 210/448 |
| 4,092,246 | 5/1978 | Kummer | 210/504 |
| 4,111,199 | 9/1978 | Djerassi | 604/6 |
| 4,115,277 | 9/1978 | Swank | 210/436 |
| 4,116,845 | 9/1978 | Swank | 210/446 |
| 4,157,967 | 6/1979 | Meyst et al. | 210/489 |
| 4,170,056 | 10/1979 | Meyst et al. | 210/446 |
| 4,187,979 | 2/1980 | Cullis et al. | 494/37 |
| 4,229,309 | 10/1980 | Cheng et al. | 428/489 |
| 4,246,107 | 1/1981 | Takenaka et al. | 210/259 |
| 4,283,289 | 8/1981 | Meyst et al. | 210/448 |
| 4,294,594 | 10/1981 | Sloane, Jr. et al. | 210/446 |
| 4,322,298 | 3/1982 | Persidsky | 210/787 |
| 4,330,410 | 5/1982 | Takenaka et al. | 210/767 |
| 4,334,901 | 6/1982 | Ayes et al. | 55/487 |

(List continued on next page.)

FOREIGN PATENT DOCUMENTS

| | | |
|---|---|---|
| 370584 | 5/1990 | European Pat. Off. |
| 446713 | 9/1991 | European Pat. Off. |
| 455215 | 11/1991 | European Pat. Off. |
| 2511872 | 3/1983 | France |
| 2735179 | 2/1978 | Germany |
| 114281 | 8/1984 | Germany |
| 1501665 | 2/1978 | United Kingdom |
| 2017713 | 10/1979 | United Kingdom |
| 2231282 | 11/1990 | United Kingdom |
| 9104088 | 4/1991 | WIPO |

*Primary Examiner*—Robert A. Dawson
*Assistant Examiner*—Sun Uk Kim
*Attorney, Agent, or Firm*—Leydig, Voit & Mayer

[57] ABSTRACT

The invention provides processing donated blood, particularly a platelet-containing solution such as platelet-containing plasma, involving separating blood into a red cell containing sediment layer and a supernatant layer, and passing the supernatant layer through a filter until the filter is blocked, thereby leaving platelets to be harvested. The preferred filter comprises a porous medium having a plurality of zones of progressively increasing density.

33 Claims, 2 Drawing Sheets

U.S. PATENT DOCUMENTS

| | | | |
|---|---|---|---|
| 4,370,381 | 1/1983 | Horikoshi et al. | 210/508 |
| 4,376,675 | 3/1983 | Perrotta | 210/509 |
| 4,416,777 | 11/1983 | Kuroda et al. | 210/446 |
| 4,422,939 | 12/1983 | Sharp et al. | 210/445 |
| 4,443,492 | 4/1984 | Roller | 604/378 |
| 4,447,220 | 5/1984 | Eberle | 494/26 |
| 4,459,210 | 7/1984 | Murakami et al. | 428/398 |
| 4,464,167 | 8/1984 | Schoendorfer et al. | 604/6 |
| 4,476,023 | 10/1984 | Horikoshi et al. | 210/446 |
| 4,477,575 | 10/1984 | Vogel et al. | 210/509 |
| 4,534,757 | 8/1985 | Geller | 604/85 |
| 4,543,084 | 9/1985 | Bailey | 494/20 |
| 4,596,657 | 6/1986 | Wisdom | 210/206 |
| 4,608,173 | 8/1986 | Watanabe et al. | 210/502.1 |
| 4,608,178 | 8/1986 | Johansson et al. | 210/744 |
| 4,617,124 | 10/1986 | Pall et al. | 210/508 |
| 4,618,533 | 10/1986 | Steuck | 428/315.7 |
| 4,620,932 | 11/1986 | Howery | 210/490 |
| 4,636,312 | 1/1987 | Willis | 210/416.1 |
| 4,663,032 | 5/1987 | Loos et al. | 210/97 |
| 4,663,058 | 5/1987 | Wells et al. | 210/801 |
| 4,675,117 | 6/1987 | Neumann et al. | 210/789 |
| 4,680,025 | 7/1987 | Kruger et al. | 604/6 |
| 4,687,580 | 8/1987 | Malbrancq et al. | 210/651 |
| 4,701,267 | 10/1987 | Watanabe et al. | 210/491 |
| 4,702,947 | 10/1987 | Pall et al. | 210/508 |
| 4,714,457 | 12/1987 | Alterbaum | 494/20 |
| 4,720,284 | 1/1988 | McCarty | 494/45 |
| 4,747,952 | 5/1988 | Nakano et al. | 210/782 |
| 4,753,739 | 6/1988 | Noble | 210/787 |
| 4,767,531 | 8/1988 | Wisdom | 210/749 |
| 4,776,964 | 3/1988 | Schoendorfer et al. | 210/782 |
| 4,786,603 | 11/1988 | Wielinger et al. | 210/500.24 |
| 4,810,378 | 3/1989 | Carmen et al. | 210/206 |
| 4,816,224 | 3/1989 | Vogel et al. | 210/767 |
| 4,833,087 | 5/1989 | Hinckley | 422/101 |
| 4,855,063 | 8/1989 | Carmen et al. | 210/749 |
| 4,880,548 | 11/1989 | Pall et al. | 210/435 |
| 4,883,764 | 11/1989 | Kloepfer | 422/56 |
| 4,892,668 | 1/1990 | Harmony et al. | 210/782 |
| 4,909,949 | 3/1990 | Harmony et al. | 210/787 |
| 4,915,848 | 4/1990 | Carmen et al. | 210/782 |
| 4,919,823 | 4/1990 | Wisdom | 210/787 |
| 4,923,620 | 5/1990 | Pall | 210/767 |
| 4,925,572 | 5/1990 | Pall | 210/767 |
| 4,933,092 | 6/1990 | Aunet et al. | 210/510.1 |
| 4,936,993 | 6/1990 | Nomura | 210/446 |
| 4,936,998 | 6/1990 | Nishimura et al. | 210/496 |
| 4,943,287 | 7/1990 | Carmen | 604/408 |
| 4,985,153 | 1/1991 | Kuroda et al. | 210/782 |
| 4,987,085 | 1/1991 | Allen et al. | 422/56 |
| 4,997,577 | 3/1991 | Stewart | 210/767 |
| 5,100,564 | 3/1992 | Pall et al. | 210/767 |
| 5,152,905 | 10/1992 | Pall et al. | 210/767 |
| 5,217,627 | 6/1993 | Pall et al. | 210/767 |
| 5,229,012 | 7/1993 | Pall et al. | 210/767 |

FILTER FOR OBTAINING PLATELETS

This application is a divisional of U.S. application Ser. No. 07/846,587, filed Mar. 5, 1992, now U.S. Pat. No. 5,258,126, which is a continuation-in-part of U.S. application Ser. No. 07/609,574, filed on Nov. 6, 1990, now U.S. Pat. No. 5,152,905, which is a continuation-in-part of U.S. application Ser. No. 07/405,977, filed on Sep. 12, 1989 (abandoned), and a continuation-in-part of U.S. application Ser. No. 07/609,654, filed on Nov. 6, 1990 (issued as U.S. Pat. No. 5,100,564).

TECHNICAL FIELD OF THE INVENTION

The present invention relates to an apparatus for processing blood donated for the purpose of therapeutic transfusion of blood components and, particularly, to improved apparatuses for harvesting platelets from donated whole blood.

BACKGROUND OF THE INVENTION

The development of plastic blood collection bags facilitated the separation of donated whole blood into its various components, e.g., platelet concentrate (hereinafter "PC"), packed red cells (hereinafter "PRC"), and plasma, thereby making platelet concentrates available as a transfusion product. The separation of a single unit of donated whole blood, about 450 milliliter in USA practice, into its components is typically accomplished by use of differential sedimentation.

A typical procedure used in the U.S., the citrate-phosphate-dextrose-adenine (CPDA-1) system, utilizes a series of steps to separate donated blood into three components, each component having substantial therapeutic and monetary value. The procedure typically utilizes a blood collection bag which is integrally attached via tubing to at least one, and preferably two or more, satellite bags. Whole blood may be thus collected and processed as follows:

(1) The donated whole blood is collected from the donor's vein directly into the blood collection bag which contains the nutrient and anti-coagulant containing CPDA-1.

(2) The blood collection bag is centrifuged together with its satellite bags, thereby concentrating the red cells as packed red cells (hereinafter PRC) in the lower portion of the blood collection bag and leaving in the upper portion of the bag a suspension of platelets in clear plasma, which is known as platelet-rich plasma (PRP).

(3) The blood collection bag is transferred, with care not to disturb the interface between the supernatant PRP layer and the sedimented PRC layer, into a device known as a "plasma extractor" which comprises an opaque back plate and a transparent front plate; the two plates are hinged together at their lower ends and spring biased toward each other such that a pressure of about 90 millimeters of mercury is developed within the bag.

With the blood collection bag positioned between the two plates, a valve or seal in the tubing is opened allowing the supernatant PRP to flow into a first satellite bag. As the PRP flows out of the blood collection bag, the interface with the PRC rises. The operator closely observes the position of the interface as it rises and clamps off the connecting tube when in his judgment as much PRP has been transferred as is possible, consistent with allowing no red cells to enter the first satellite bag. This is a time consuming operation during which the operator must visually monitor the bag and judiciously and arbitrarily ascertain when to shutoff the connecting tube. The blood collection bag, now containing only PRC, may be detached and stored at 4° C. until required for transfusion into a patient, or a valve or seal in the flexible tubing may be opened so that the PRC may be transferred to a satellite bag using either the pressure generated by the plasma extractor apparatus, or by placing the blood collection apparatus in a pressure cuff, or by elevation to obtain gravity flow.

(4) The PRP-containing satellite bag, together with another satellite bag, is then removed from the extractor and centrifuged at an elevated G force with the time and speed adjusted so as to concentrate the platelets into the lower portion of the PRP bag. When centrifugation is complete, the PRP bag contains sedimented platelets in its lower portion and clear plasma in its upper portion.

(5) The PRP bag is then placed in the plasma extractor, and most of the clear plasma is expressed into the other satellite bag, leaving the PRP bag containing only sedimented platelets in about 50 ml of plasma; in a subsequent step, this platelet composition is dispersed to make PC. The PRP bag, now containing a PC product, is then detached and stored for up to five days at 20°-22° C., until needed for a transfusion of platelets. For use with adult patients, the platelets from 6-10 donors are, when required, pooled into a single platelet transfusion.

(6) The plasma in the other satellite bag may itself be transfused into a patient, or it may be separated by complex processes into a variety of valuable products.

Commonly used systems other than CPDA-1 include Adsol, Nutricell, and SAG-M. In these latter systems, the collection bag contains only anticoagulant, and the nutrient solution may be preplaced in a satellite bag. This nutrient solution is transferred into the PRC after the PRP has been separated from the PRC, thereby achieving a higher yield of plasma and longer storage life for the PRC.

With the passage of time and accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

For this reason, the separation of blood into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels; associated internal and external bleeding additionally requires more frequent transfusions of PC, and this has caused platelets to be in short supply and has put pressure on blood banks to increase platelet yield per unit of blood.

Blood bank personnel have responded to the increased need for blood components by attempting to increase PC yield in a variety of ways, including attempting to express mere PRP prior to stopping flow from the blood collection bag. This has often proved to be counterproductive in that the PRP, and the PC subsequently extracted from it, are frequently contaminated by red cells, giving a pink or red color to the normally light yellow PC. The presence of red cells in PC is so highly undesirable that pink or red PC is frequently discarded, or subjected to recentrifugation, both of which increase operating costs.

The method and apparatus of the present invention alleviate the above-described problems and, in addition, provide a higher yield of superior quality PC.

In addition to the three above-listed components, whole blood contains white blood cells (known collectively as leucocytes) of various types, of which the most important are granulocytes and lymphocytes. White blood cells provide protection against bacterial and viral infection.

The transfusion of blood components which have not been leucocyte-depleted is not without risk to the patient receiving the transfusion. Chills, fever, and allergic reactions may occur in patients receiving acute as well as chronic platelet therapy. Repeated platelet transfusions frequently lead to alloimmunization against HLA antigens, as well as platelet specific antigens. This, in turn, decreases responsiveness to platelet transfusion. Leucocytes contaminating platelet concentrates, including granulocytes and lymphocytes, are associated with both febrile reactions and alloimmunization, leading to platelet transfusion refractoriness. Another life-threatening phenomenon affecting heavily immunosuppressed patients is Graft Versus Host Disease. In this clinical syndrome, donor lymphocytes transfused with the platelet preparations can launch an immunological reaction against the transfusion recipient with pathological consequences. Some of these risks are detailed in U.S. Pat. No. 4,923,620 and in U.S. Pat. 4,880,548.

In the above described centrifugal method for separating blood into the three basic fractions, the leucocytes are present in substantial quantities in both the packed red cells and platelet-rich plasma fractions. It is now generally accepted that it would be highly desirable to reduce the leucocyte concentration of these blood components to as low a level as possible. While there is no firm criterion, it is generally accepted that many of the undesirable effects of transfusion would be reduced if the leucocyte contempt were reduced by a factor of about 100 or more prior to administration to the patient. This approximates reducing the average total content of leucocytes in a single unit of PRC or PRP to less than about $1 \times 10^7$, and in a unit of PRP or PC to less than about $1 \times 10^6$.

Growing evidence suggests that the use of leucocyte depleted platelet concentrates decreases the incidence of febrile reactions and platelet refractoriness. Leucocyte depleted blood components are also believed to have a role in reducing the potential for Graft Versus Host Disease. Leucocyte depletion of platelet preparations is also believed to diminish, but not to completely prevent, the transmission of leucocyte associated viruses such as HIV-1 and CMV.

Platelet preparations contain varying amounts of leucocytes. The level of leucocyte contamination in unfiltered conventional platelet preparations of 6 to 10 pooled units is generally at a level of about $5 \times 10^8$ or greater. Platelet concentrates prepared by the differential centrifugation of blood components will have varying levels of leucocyte contamination related to the time and to the magnitude of the force developed during centrifugation. It has been demonstrated that leucocyte removal efficiencies of 81 to 85% are sufficient to reduce the incidence of febrile reactions to platelet transfusions. Several other recent studies report a reduction in alloimmunization and platelet refractoriness at levels of leucocyte contamination $<1 \times 10^7$ per unit. For a single unit of PC, the goal is to reduce the number of leucocytes from about $7 \times 10^7$ leucocytes (average leucocyte contamination level under current practice) to less than about $1 \times 10^6$ leucocytes. The existing studies therefore suggest the desirability of at least a two log (99%) reduction of leucocyte contamination. More recent studies suggest that a three log (99.9%) or even a four log (99.99%) reduction would be significantly more beneficial.

An additional desirable criterion is to restrict platelet loss to about 15% or less of the original platelet concentration. Platelets are notorious for being "sticky", an expression reflecting the tendency of platelets suspended in blood plasma to adhere to any non-physiological surface to which they are exposed. Under many circumstances, they also adhere strongly to each other.

In any system which depends upon filtration to remove leucocytes from a platelet suspension, there will be substantial contact between platelets and the internal surfaces of the filter assembly. The filter assembly must be such that the platelets have minimal adhesion to, and are not significantly adversely affected by contact with, the filter assembly's internal surfaces.

U.S. Pat. No. 4,880,548 provides a convenient and very effective means for leuco-depleting PC. PC is passed through a fibrous porous medium which permits recovery of 90% or more of the platelets, which pass through the medium, while retaining within the medium more than 99.9% of the incident leucocytes. This system is currently in widespread use at bedside in hospitals, but, unlike the device of this invention, it is not as well suited for use in blood banks during the processing of donated whole blood. The unsuitability stems primarily from additional storage constraints associated with PC and the methods of administering PC. For example, platelets in PC are typically suspended in a total volume of only about 40 to 60 ml of plasma. Contrasted with this, the platelets which are processed in accordance with this invention are typically derived from a single unit of whole blood and are suspended as PRP in about 180 to 240 ml of plasma.

Further, the platelets in PC have been subjected, during two centrifugation steps, to severe conditions and may not as readily disperse. It has been suggested that the high forces to which the platelets are subjected as they reach the bottom of the bag during sedimentation, promote increased aggregation by particle-to-particle adhesion.

For these and perhaps other reasons, platelets in PC show a much higher tendency to be retained within the filter during leucocyte depletion compared with platelets in PRP. Accordingly, a much better recovery is obtained when platelets are leucocyte-depleted in the form of PRP, compared with PC; for example, while optimal recovery from PC is about 90 to 95%, recovery from PRP can exceed 99%.

Also, as a consequence of the concentration differences and possibly as a consequence of the lower degree of aggregation in PRP, the preferred critical wetting surface tension (CWST) range when filtering PRP is broader than that for PC.

Devices which have previously been developed in attempts to meet the above-noted objectives have been based on the use of packed fibers, and have generally been referred to as filters. However, it would appear that processes utilizing filtration based on separation by size cannot succeed for two reasons. First, leucocytes can be larger than about 15 μm (e.g., granulocytes and macrocytes) to as small as 5 to 7 μm (e.g., lymphocytes). Together, granulocytes and lymphocytes represent the major proportion of all of the leucocytes in normal blood. Red blood cells are about 7 μm in diameter, i.e., they are about the same size as lymphocytes, one of the two major classes of leucocytes which must be removed. Secondly, all of these cells deform so that the are able to pass through much smaller openings than their normal size. Accordingly, it has been widely accepted that removal of leucocytes is accomplished mainly by adsorption on the internal surfaces of porous media, rather than by filtration.

The separation of the various blood components using centrifugation is attended by a number of problems. First, in the separation of platelet-rich plasma from PRC, e.g., step 3 above, it is difficult to efficiently obtain the maximum yield of platelets while preventing red cells from entering the plasma. Secondly, when PRP is expressed, it is difficult to efficiently recover the more desirable younger platelets located near or in the PRC/PRP interface.

BRIEF SUMMARY OF THE INVENTION

In accordance with this invention, leucocyte depletion is preferably accomplished at the time the blood is processed. During the separation of PRP from PRC, the process may be enhanced by interposing a red cell barrier medium immediately downstream of the blood collection bag. Thus, the supernatant PRP passes through a porous medium until red cells block the medium. The platelet-containing solution such as PRP may be subsequently centrifuged to obtain a supernatant leucocyte-depleted plasma layer and a sediment leucocyte-depleted PC layer. The apparatus of the present invention permit the recovery of an increased amount of more desirable platelets and of plasma more efficiently in comparison to conventional blood processing practices.

BRIEF DESCRIPTION OF THE DRAWINGS

FIG. 1 is a cross section view of an embodiment of a red cell barrier filter assembly, taken along A—A of FIG. 2a.

DETAILED DESCRIPTION OF THE PREFERRED EMBODIMENTS

The present invention involves harvesting an increased amount of platelets from a platelet-containing solution, particularly PRP, which comprises separating a red cell containing biological fluid such as whole blood into a red cell-containing sediment layer and a non-red cell containing supernatant layer, and passing the supernatant layer of the separated fluid through a filter until red cells block the filter. An increased amount of platelets and/or plasma may then be recovered. The present invention also involves an apparatus which permits the increased recovery of platelets comprising a porous medium which passes platelets and/or plasma therethrough, but blocks the passage of red cells. The present invention also involves a system for harvesting an increased amount of platelets and/or plasma which comprises a first container in fluid communication with second container, and, interposed between the first container and the second container, a red cell barrier medium.

Figure 1:
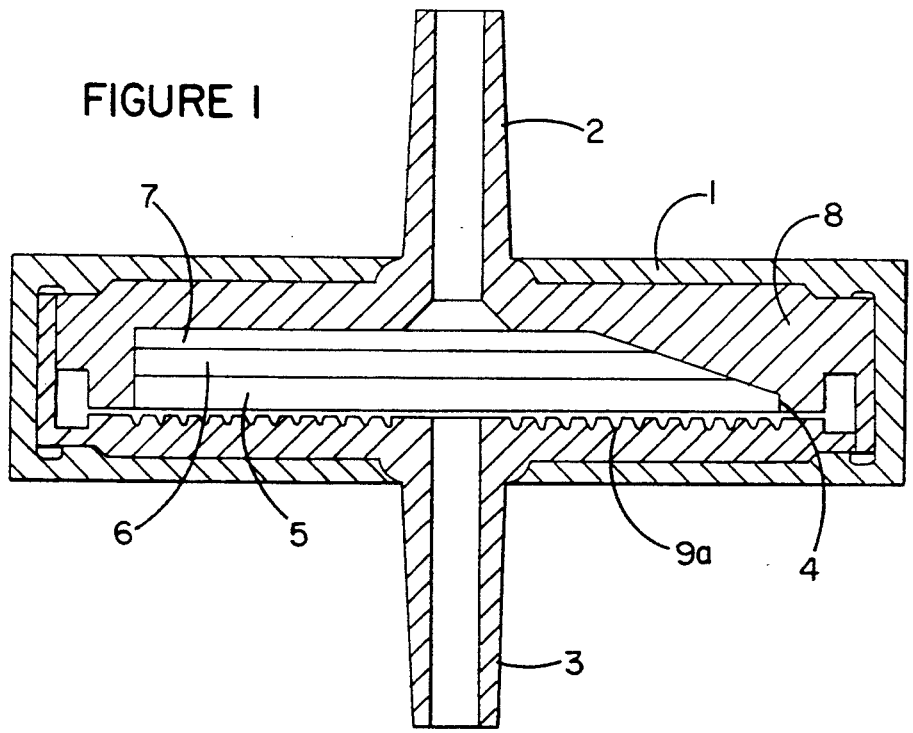

An exemplary biological fluid red cell barrier filter assembly is shown in FIGS. 1 and 2. A red cell barrier filter assembly may include a housing 1 having an inlet 2 and an outlet 3 and defining a liquid flow path between the inlet and the outlet. A red cell barrier medium 4, preferably positioned inside the housing across the liquid flow path, includes a porous medium which permits a platelet-containing solution such as PRP to pass therethrough, but blocks the passage of red cells. In a preferred embodiment, flow through the filter assembly is stopped automatically when red cells contact the red cell barrier medium.

While the red cell barrier medium can be produced from any suitable material compatible with a biological fluid such as blood, practical considerations dictate that consideration be given first to the use of commercially available materials. The porous medium of this invention may be formed, for example, from any synthetic polymer capable of forming fibers and of serving as a substrate for grafting. Preferably, the polymer should be capable of reacting with at least one ethylenically unsaturated monomer under the influence of ionizing radiation without the matrix being significantly or excessively adversely affected by the radiation. Suitable polymers for use as the substrate include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene fluoride, polyethylene, polypropylene, cellulose acetate, and Nylon 6 and 66. Preferred polymers are polyolefins, polyesters, and polyamides. The most preferred polymer is polybutylene terephthalate (PBT).

Although the fibers of the porous medium may remain untreated, they are preferably treated to make them even more effective. For example, the fibers may be surface modified to increase the critical wetting surface tension (CWST) of the fibers.

Surface characteristics of a fiber can be modified by a number of methods, for example, by chemical reaction including wet or dry oxidation, by coating the surface by depositing a polymer thereon, by grafting reactions which are activated by exposure to an energy source such as gas plasma, heat, a Van der Graff generator, ultraviolet light, or to various other forms of radiation, or by surface etching or deposition using a gas plasma treatment. The preferred method is a grafting reaction using gamma-radiation, for example, from a cobalt source.

In a preferred form of the porous medium of the subject invention, the fibers of which the filter element is composed may be modified by grafting thereon a mixture of two monomers, one containing hydroxyl groups and another containing anionic groups, such as carboxyl groups, with the hydroxyl groups present in larger numbers. As described in U.S. Pat. No. 4,880,548, the filter media of this invention are preferably surface modified using a mixture comprising hydroxyl-terminated and carboxyl-terminated monomers. In a preferred form of this invention, the monomers are respectively hydroxyethyl methacrylate (HEMA) and methacrylic acid (MAA), and the monomer ratios (carboxyl:hydroxyl) are preferably in the range of about 0.01:1 to about 0.5:1, and more preferably in the range of about 0.05:1 to about 0.35:1. A preferred monomer ratio is one which produces a desired zeta potential at the pH of plasma (7.3) of about $-3$ to about $-30$ millivolts, a more preferred ratio produces a zeta potential of about $-7$ to about $-20$ millivolts, and a still more preferred ratio produces a zeta potential of about $-10$ to about $-14$ millivolts.

Radiation grafting, when carried out under appropriate conditions, has the advantage of considerable flexibility in the choice of reactants, surfaces, and in the methods for activating the required reaction. Gamma-radiation grafting is particularly preferable because the products are very stable and have undetectably low aqueous extractable levels. Furthermore, the ability to prepare synthetic organic fibrous media having a CWST within a desired range is more readily accomplished using a gamma radiation grafting technique.

An exemplary radiation grafting technique may employ at least one of a variety of monomers each comprising an ethylene or acrylic moiety and a second group, which can be selected from hydrophilic groups (e.g., —COOH, or —OH). Grafting of the fibrous medium may also be accomplished by compounds containing an ethylenically unsaturated group, such as an acrylic moiety, con,Dined with a hydroxyl group, preferably monomers such as HEMA or acrylic acid. The compounds containing an ethylenically unsaturated group may be combined with a second monomer such as MAA. Use of HEMA as the monomer contributes to a very high CWST. Analogues with similar functional characteristics may also be used to modify the surface characteristics of fibers.

The number of carboxyl groups per unit of surface area appears to have an important effect on the adhesion of platelets to fiber surfaces. This effect is reflected in the proportion of platelets recovered in the filter effluent as a fraction of the number present prior to filtration. Platelet recovery typically peaks at the optimum proportion of MAA. The number of carboxyl groups per unit of fiber surface is, over the range of interest of this invention, thought to be close to proportional to the amount of MAA in the monomeric grafting solution.

The CWST of the porous media made with the PBT fibers typically have a CWST as formed of about 50 to about 54 dynes/cm, and most or all other fibers which may be used have a CWST below about 55 dynes/cm. Surface grafting using the monomers noted above causes the CWST of the fibers to increase, the exact value obtained being dependent on the ratio of the two monomers. A preferred range for the CWST of the devices of this invention is greater than about 70 dynes/cm, typically from about 70 dynes/cm to about 115 dynes/cm more preferred range is about 90 to about 100 dynes/cm and a still more preferred range is about 93 to about 97 dynes/cm, these ranges being obtained by varying the ratio of carboxylterminated and hydroxyl-terminated monomers.

As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Liquids with surface tensions lower than the CWST of a porous medium will spontaneously wet the medium on contact and, if the medium has through holes, will flow through it readily. Liquids with surface tensions higher than the CWST of the porous medium may not flow at all at low differential pressures and may do so unevenly at sufficiently high differential pressures to force the liquid through the porous medium. In order to achieve adequate priming of a fibrous medium with a liquid such as blood, the fibrous medium preferably has a CWST in the range of about 53 dynes/cm or higher.

A red cell barrier filter assembly produced in accordance with the present invention and suitable for passing about one unit of PRP preferably has a fiber surface area of about 0.04 to about $3.0M^2$, more preferably about 0.06 to about $2.0M^2$. A preferred range for the filter element flow area is about 3 to about 8 cm$^2$, more preferably about 4 to about 6 cm$^2$. A preferred range for the relative voids volume is about 71% to about 83% (corresponding for PBT fibers to a density of about 023 to about 0.40 g/cc), more preferably about 73% to about 80% (about 0.27 to about 0.37 g/cc). Because of its small size, a preferred filter in accordance with the present invention retains internally only about 0.5 to 1 cc of PRP, representing less than a 0.5% loss of platelets.

In another embodiment of the invention, the fiber may be surface modified in the same manner as noted above, but the fiber surface area of the element is increased while, at the same time, the density of the filter element is somewhat reduced. In this way, the automatic blockage of flow on contact by red cells is combined with higher efficiency of leucocyte depletion.

A preferred range of fiber surface area for this embodiment of the invention is from about 0.3 to about $2.0M^2$, and a more preferred range is from about 0.35 to about $0.6M^2$. The upper limits of fiber surface area reflect the desire to accomplish the filtration in a relatively short time period, and may be increased if longer filtration times are acceptable. A preferred voids volume of a porous medium of this embodiment is in the range of about 71% to about 83% (i.e., if PBT fiber is used, corresponding to a density of the filter element in the range of about 0.23 g/cc to about 0.40 g/cc), and more preferably about 75% to about 80% (for PBT, about 0.28 g/cc to about 0.35 g/cc). A preferred filter element flow area is from about 2.5 to about 10 cm$^2$, and a more preferred area is from about 3 to about 6 cm$^2$. The upper limits of the filter element flow area reflect the desire to accomplish the filtration in a relatively short time period, and may be increased if longer filtration times are acceptable. Leucocyte depletion efficiencies in excess of about 99.9 to about 99.99%, which corresponds to an average residual leucocyte content per unit of less than about $0.005 \times 10^7$, can be obtained.

Although the porous medium of the present invention may have a substantially uniform density, the porous medium of a preferred embodiment of the present invention is of a construction such that an upstream portion of the porous medium is of generally lower density than a (downstream portion of the filter. For example, the density of the porous medium may vary in a continuous or stepwise manner while maintaining an average density range suitable for blocking red cells. An exemplary porous medium may include a density range in the upstream portion from about 0.1 g/cc to about 0.23 g/cc, and a density range in the downstream portion from about 0.23 g/cc to about 0.40 g/cc. In another embodiment of the invention, the porous medium may include two or more layers, preferably of different or varying density. An exemplary zoned or layered medium is illustrated in FIG. 1; using PBT as the fiber upstream layer 5 may include a density range from about 0.1 g/cc to about 0.2 g/cc, middle layer 6 may include a density range from about 0.20 g/cc to about 0.25 g/cc, and downstream layer 7 may include a density range from about 0.23 g/cc to about 0.40 g/cc.

Included within the scope of the present invention are the use of other density valves, in a particular zone or layer as well as throughout the porous medium. These alternative density ranges may be chosen based on achieving a desired result, in addition to blocking red cells, e.g., the flow rate, the type of fiber used, the amount of leucocytes removed, as well as other considerations.

The porous medium may act as an automatic "valve" by instantly stopping the flow of the supernatant layer of the centrifuged whole blood, which supernatant layer will typically be a platelet-rich solution such as PRP, when red cells from the sediment layer, typically a red cell containing solution such as PRC, contact the porous medium. The mechanism of this valve-like action may reflect aggregation of the red cells concentrated at the PRP/PRC transition zone (buffy coat) as they reach the medium's surface, forming a barrier which prevents or blocks further flow of the supernatant layer through the porous medium. Aggregation of red blood cells on contact with the porous medium appears to be related to the CWST and/or to other less understood surface characteristics of the fibers. This theory for the proposed mechanism is supported by the existence of filters capable of highly efficient leucocyte depletion of human red blood cell suspensions and which have pore sizes as small as 0.5 $\mu$m, through which red cells pass freely and completely with no clogging, with applied pressure of the same magnitude as that used in the present invention. On the other hand, the filters of the present invention, which typically have pore diameters larger than about 0.5 $\mu$m, abruptly stop the flow of red blood cells when the porous medium is contacted by the red cells.

Housings for the filter assembly to be used in conjunction with the present invention can be fabricated from any suitably impervious material, including an impervious thermoplastic material. For example, the housing may preferably be fabricated by injection molding from a transparent or translucent polymer, such as an acrylic, polystyrene, or polycarbonate resin. Not only is such a housing easily and economically fabricated, but it also allows observation of the passage of the fluid through the housing.

Figure 2A:
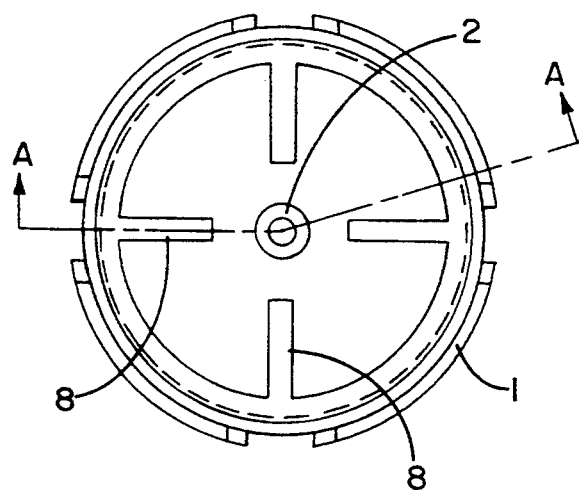
FIG. 2a is a top view of an embodiment of a red cell barrier filter assembly according to the invention.
Figure 2B:
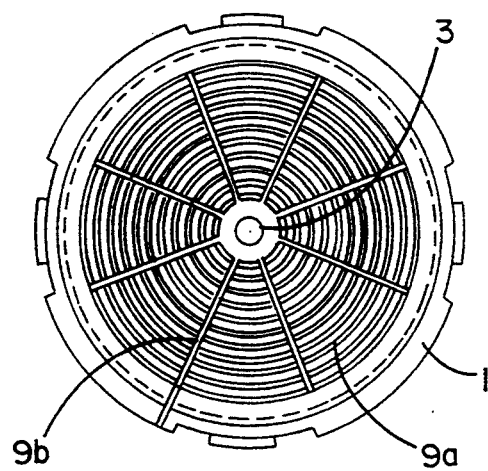
FIG. 2b is a bottom view of an embodiment of a red cell barrier filter assembly according to the invention.

Any housing of suitable shape, preferably providing an inlet and an outlet, may be employed. The housing may include an arrangement of one or more channels, grooves, conduits, passages, ribs, or the like, which may be serpentine, parallel, curved, circular, or a variety of other configurations. An exemplary embodiment is shown in FIGS. 2A and 2B, illustrating a circular housing 1 having an inlet 2 and an outlet 3. A preferred embodiment of the invention includes one or more ribs 8 on the upstream side of the housing and at least one channel or groove on the downstream side of the housing. In a most preferred embodiment of the invention, the housing 1 includes a series of concentric grooves or channels 9a and radial grooves or channels 9b which provide fluid communication with the outlet 3.

The housing into which the porous medium is placed may be sealed or interference fit, and is designed to achieve practical and economic construction, convenience of use, rapid priming, and efficient air clearance.

The porous components of devices made in accordance with the invention are preferably preformed prior to assembly to controlled dimension and pore diameter in order to form an integral self-contained element.

Preforming eliminates the pressure on the inlet and outlet faces of the container which are inherent in a packed fiber system. Pre-forming the porous element typically leads to devices having longer service life, coupled with at least equal and usually better leucocyte removal efficiency, equal or better platelet recovery, and less hold up of fluid, when compared to devices that use fibers or fibrous webs packed into a housing at assembly.

Furthermore, pre-forming enhances the proper positioning of the porous medium in the housing. The lateral dimensions of the porous element are typically larger than the corresponding dimensions of the housing into which they are assembled. For example, if the porous medium is in disc form, the outside diameter of the pre-formed medium is made about 1% larger than the housing inside diameter. This provides very effective sealing by an interference fit with no loss of effective area of the porous medium, and contributes further towards minimization of the fluid hold-up volume of the assembly. In accordance with the invention, assembling the porous medium in the housing using an interference fit seal is preferred. However, edge compression about the periphery, a compression seal, or other means of positioning the porous medium in the housing may be used.

Included within the scope of the present invention is the inclusion of the red cell barrier medium or filter assembly in biological fluid processing systems, preferably closed, sterile systems, having a wide variety of components, such as one or more biological fluid collection bags; one or more satellite bags; gas or air inlets and outlets; and/or one or more connectors, such as SCD connectors.

Figure 3:
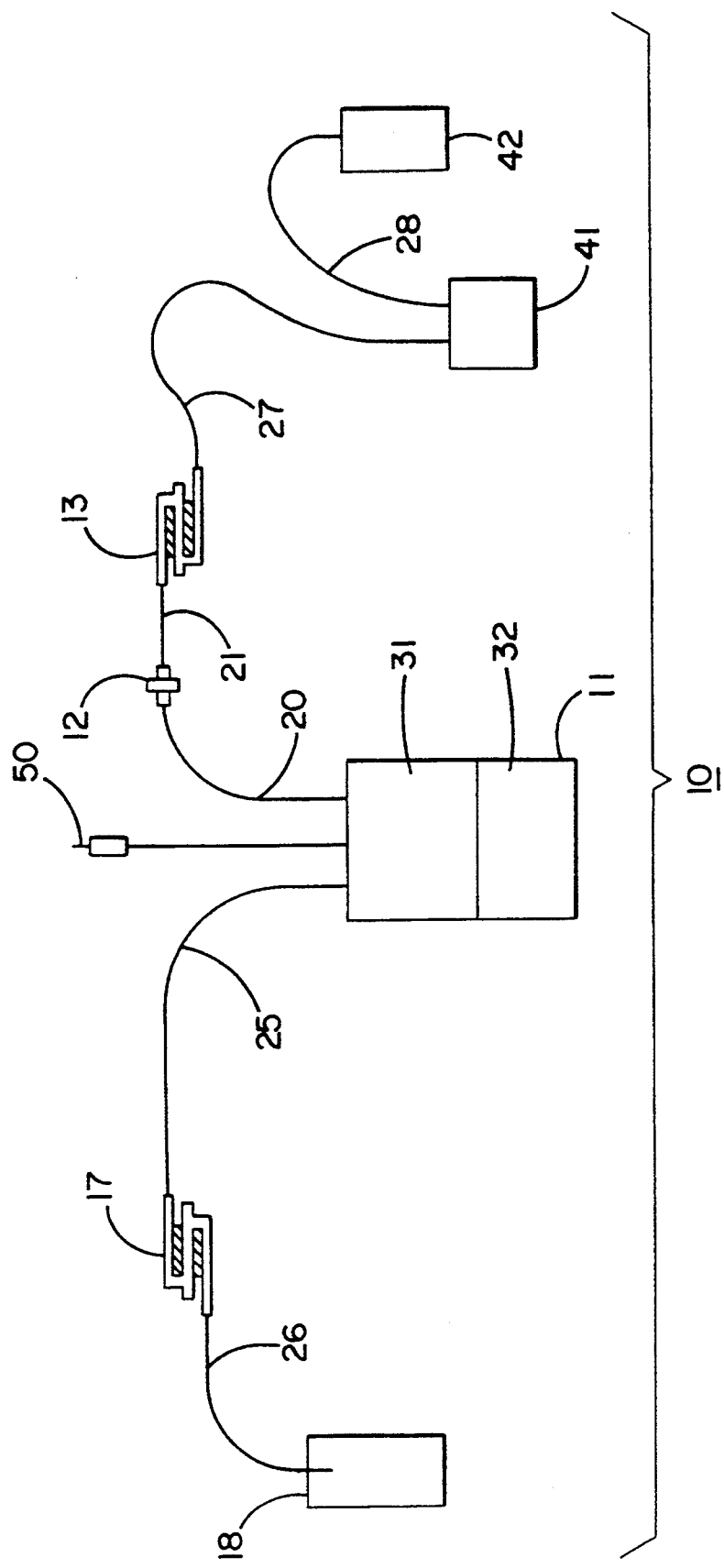
FIG. 3 is an embodiment of a biological fluid processing system according to the invention, whereby a red cell barrier filter assembly is interposed between a collection container and a satellite bag.

An exemplary biological fluid collection and processing system is shown in FIG. 3. The biological fluid processing system is generally denoted as 10. It may comprise a first container or collection bag 11; a needle or cannula 50 adapted to be inserted into the donor; a red cell barrier filter assembly 12; a first leucocyte depletion assembly 13 (optional); a second container (first satellite bag) 41, typically for receiving a platelet-rich solution or suspension 31; an optional fourth container (third satellite bag) 42, typically for receiving platelet concentrate; a second leucocyte depletion assembly 17; and a third container (second satellite bag) 18, typically for receiving a red cell containing solution or suspension 32. Each of the assemblies or containers may be in fluid communication through tubing, preferably flexible tubing, 20, 21, 25, 26, 27 or 28. The first leucocyte depletion assembly preferably includes a porous medium for passing PRP; the second leucocyte depletion assembly preferably includes a porous medium suitable for passing PRC. A seal, valve, clamp, or transfer leg closure (not illustrated) may also be positioned in or on the tubing or in the collection and/or satellite bags. The seal (or seals) is opened when fluid is to be transferred between bags.

The invention also involves processing a biological fluid containing red blood cells comprising collecting whole blood in a container; forming a supernatant layer and a sediment layer, typically by differential sedimentation such is centrifugation; and passing the supernatant layer through a porous medium, the porous medium comprising a red cell barrier medium or a combined leucocyte depletion red cell barrier medium. The supernatant layer passes through the porous medium until red cells contact the porous medium, at which point flow through the medium stops automatically.

In general, donated whole blood is processed as soon as practicable in order to more effectively reduce or eliminate contaminating factors, including but not limited to leucocytes and microaggregates. In accordance with the subject invention, leucocyte depletion may be accomplished during the initial processing of the whole blood, which in U.S. practice is generally within 8 hours of collection from the donor. After the cellular component of whole blood, i.e., red cells, have separated, the liquid portion, i.e. supernatant PRP, is expressed from the blood collection bag into a first satellite bag through one or more porous media which diminish the amount of leucocytes and/or block red cells.

In general, using the Figures for reference, the biological fluid (e.g., donor's whole blood) is received directly into the collection bag 11. The collection bag 11, with or without the other elements of the system, may then be centrifuged in order to separate the biological fluid into a supernatant layer, typically a platelet-containing solution such as PRP, and a sediment layer, typically a red cell solution such as PRC. The biological fluid may be expressed from the collection bag as separate supernatant and sediment layers, respectively. There may be a clamp or the like on or in the bag or tubing to prevent the flow of the supernatant layer from entering the wrong conduit.

Movement of the biological fluid through the system is effected by maintaining a pressure differential between the collection bag and the destination of the biological fluid (e.g., a container such as a satellite bag). Exemplary means of establishing this pressure differential may be by expressor, gravity head, applying pressure to the collection bag (e.g., by hand or with a pressure cuff), or by placing the other container (e.g., satellite bag) in a chamber (e.g., a vacuum chamber) which establishes a pressure differential between the collection bag and the other container. Also included within the scope of the invention may be expressors which generate substantially equal pressure over the entire collection bag.

As the biological fluid passes from one bag to the next, it may pass through at least one porous medium. Typically, if the biological fluid is the supernatant layer (e.g., PRP), it may pass from the collection bag through one or more devices or assemblies comprising one or more porous media—a leucocyte-depletion medium, a red cell barrier medium, a porous medium which combines the red cell barrier with leucocyte depletion in one porous medium, or a leucocyte depletion medium and a red cell barrier medium in series. The supernatant layer is expressed from the first container 11 until flow is stopped. Additional processing, if desired, may occur downstream of the red cell barrier medium, either connected to the system or after being separated from the system.

In accordance with an additional embodiment of the invention, the recovery of various biological fluids is maximized. Recovery of an increased amount of PRP in and of itself may increase the amount of platelets recovered. Furthermore, recovering a greater amount of the platelets located in or near the PRP/PRC interface may increase the recovery of the more useful and/or more desirable younger platelets.

The advantages to be gained by the use of the methods and devices of the invention include the following:

(a) The PC derived from the PRP is substantially free of red cells, and may include a higher proportion of younger platelets.

(b) The operator needs only to start the flow of platelet-rich solution, which will continue to flow into the first satellite bag until red cells contact the filter surface, at which point flow stops automatically. This eliminates the need for a skilled operator to estimate when to stop flow and decreases the possibility of red cell contamination.

(c) The volume of plasma add PC recovered from the blood collection bag during the extraction operation may be increased by about 5% or more when compared with very competent manual operation, and the concentration of platelets recovered may be increased by about 15% to about 30% or more.

(d) About 90% or greater of the platelets in whole blood are recovered.

(e) Labor input is reduced, as monitoring of the interface during decantation is not required.

(f) Freshly donated blood contains platelets varying in age from newly formed to nine days or more (platelet half-life in vivo is about nine days). Newly formed platelets are larger and are generally believed to be more active. Because the younger platelets are larger, they tend to sediment faster during centrifugation and, consequently, are present in larger numbers in the PRP nearest to the red cell interface. Measurements have shown that the concentration of platelets in the 10% of the PRP volume nearest the interface is about twice that in the uppermost 10% of PRP. Taking this into account, the total number of platelets recovered may be increased by about 4 to 10%.

|  | Incremental number of platelets, % |
| --- | --- |
| Due to increased volume of PRP | 2 to 5 |
| Due to the higher concentration of platelets in the incremental volume of PRP | 2 to 5 |
| Total | 4 to 10% |

(g) The larger proportion of younger platelets in the PC administered to the patient means that their life within the patient after administration will be longer and that the platelets will be more active, compared with current blood bank practice.

(h) The yield of plasma, a component of value comparable with that of PRC and PC, may also increased by about 2 to about 5%.

(i) Insofar as the plasma yield is increased, the plasma content of the PRC is decreased. This is advantageous because the MHC (major histocompatibility complex)

contained in the plasma is responsible for the occurrence of Urticaria (hives) in a proportion of transfusion recipients transfused with PRC.

Definitions: The following definitions are used in reference to the invention:

A) Blood Product or Biological Fluid: anticoagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. Blood product or biological fluid also includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), platelet-free plasma, platelet-poor plasma, plasma, packed red cells (PRC), or buffy coat; analogous blood products derived from blood or a blood component or derived from bone marrow. The biological fluid may include leucocytes, or may be treated to remove leucocytes. As used herein, blood component or product refers to the components described above, and to similar blood products obtained by other means and with similar properties. In accordance with the invention, each of these blood products is processed in the manner described herein.

B) Unit of Whole Blood: blood banks in the U.S. commonly draw about 450 milliliters (ml) of blood from the donor into a bag which contains an anticoagulant to prevent the blood from clotting. However, the amount drawn differs from patient to patient and donation to donation. Herein the quantity drawn during such a donation is defined as a unit of whole blood.

C) Unit of Packed Red Cells (PRC), Plateletrich Plasma (PRP), or Platelet Concentrate (PC): As used herein, a "unit" is defined by the U.S. practice, and a unit of PRC, PRP, PC, or of red cells or platelets in physiological fluid or plasma, is the quantity derived from one unit of whole blood. Typically, the volume of a unit varies. For example, the volume of a unit of PRC varies considerably dependent on the hematocrit (percent by volume of red cells) of the drawn whole blood, which is usually in the range of about 37% to about 54%. The concomitant hematocrit of PRC, which varies over the range from about 50 to over 80%, depends in part on whether the yield of one or another blood product is to be minimized. Most PRC units are in the range of about 170 to about 350 ml, but variation below and above these figures is not uncommon.

D) Porous medium: refers to the porous medium through which one or more blood components pass. The porous medium refers generically to any one of the media which deplete leucocytes from the non-PRC blood components, i.e., from PRP or from PC and/or which block the passage of red cells while allowing the passage of platelets and plasma.

The porous medium for use with a platelet-rich solution such as PRP may be formed from any natural or synthetic fiber or other porous material compatible with blood. Preferably, the CWST and zeta potential of the porous medium are within certain ranges, as disclosed above and as dictated by its intended use. For example, the CWST of a PRP porous medium is typically above about 70 dynes/cm.

The porous medium may be configured as a flat sheet, a composite of two or more layers, a corrugated sheet, a web, a fibrous mat, a depth filter or a membrane, although it is not intended that the invention should be limited thereby.

E) Voids volume is the total volume of all of the pores within a porous medium. Voids volume is expressed hereinafter as a percentage of the apparent volume of the porous medium.

F) Conversion of density when using fibers other than PBT: In the preceding exposition the term density has been used, and the density values quoted for the filter element have been based on the use of PBT fibers. Other fibers which differ in density from the PBT may be used, as noted above, providing that their surfaces have, or have been modified to have, the characteristics noted above, e.g., a CWST of greater than 70 dynes/cm. In accordance with the invention, to use an alternate fiber of different density, the density of an element made using an alternate fiber (i.e., the PBT equivalent density) may be calculated as follows:

Denoting V as a percentage of the voids volume relative to the apparent volume of the PBT element [i.e., V=(volume of voids/volume of element)×100], the objective is to calculate the element density of an alternate fiber element which will have a relative voids volume percentage equal to V.

If F is the density of the alternate fiber and 1.38 g/cc is taken as the density of PBT fiber, and $M_1$ is the element density of the PBT element and $M_2$ is the density required for an element with equivalent performance, then voids volume V of the PBT fiber element is $$V=(1-M_1/1.38)\times 100$$

and the density required for the element made using the alternate fiber is $$M_2=F(1-V/100).$$

The more preferred fiber diameter range for the practice of this invention is about 2 to 3 μm, the diameter being defined in terms of surface area, as described in U.S. Pat. No. 4,880,548. This range is preferred because much above this range, the dimensions of the elements and consequently the liquid hold-up volumes of the filters become significantly larger; below this range, the filter elements become relatively less coherent and are more easily compressed. For example, an element made using less than 2 μm polypropylene fibers would be compressed by the pressure developed by the plasma extractor, which can be as high as 300 mm of Hg.

Pore diameters of filter elements in accordance with the invention can be determined using the modified OSU F2 method as described in U.S. Pat. No. 4,925,572. Filter assemblies with good efficiency and recovery can be made using large pore diameters, but such filter assemblies typically retain a higher proportion of platelets. A filter assembly having a pore diameter of about 15 μm to 30 μm or higher may allow some red cells and leucocytes to pass, thereby reducing platelet recovery efficiency. Therefore, it is preferred that the pore diameter not exceed 15 μm, more preferably, less than about 10 μm. The most preferred pore diameter range is less than about 6 μm.

G) In accordance with the invention, a useful technique for the measurement of fiber surface area, for example by nitrogen gas adsorption, is that developed by Brunauer, Emmet, and Teller in the 1930's, often referred to as the "BET" measurement. Using PBT as an example, the surface area of meltblown webs can be used to calculate average fiber diameter:

$$\text{Total volume of fiber in 1 gram} = \frac{1}{1.38} \text{ cc}$$

(where 1.38 = fiber density of PBT, g/cc)

$$\text{hence } \frac{\pi d^2 L}{4} = \frac{1}{1.38} \quad (1)$$

Area of the fiber is $\pi d L = A_f$ (2)

Dividing (1) by (2), $\frac{d}{4} = \frac{1}{1.38 A_f}$ and $d = \frac{4}{1.38 A_f} = \frac{2.9}{A_f}$, or $(0.345 A_f)^{-1}$ where L=total length in cm of 1 gram of fiber,
d=average fiber diameter in centimeters, and
$A_f$=fiber surface area in cm²/g. If the units of d are micrometers, the units of $A_f$ become M²/g (square meters/gram), which will be used hereinafter. For fibers other than PBT, substitute the density for 1.38.

H) General procedure for measuring zeta potential: geta potential was measured using a sample cut from a ½ inch thick stack of webs.

The zeta potential was measured by placing the sample in an acrylic filter holder which held the sample snugly between two platinum wire screens 100×100 mesh (i.e., 100 wires in each direction per inch). The meshes were connected, using copper wire, to the terminals of a Triplett Corporation model 3360 Volt-Ohm Meter, the mesh on the upstream side of the sample being connected to the positive terminal of the meter. A pH-buffered solution was flowed through the sample using a differential pressure of 45 inches of water column across the filter holder and the effluent was collected. For measurements at pH 7, a buffered solution was made by adding 6 ml pH 7 buffer (Fisher Scientific Co. catalog number SB108-500) and 5 ml pH 7.4 buffer (Fisher Scientific Co. catalog number SB1100500) to 1 liter pyrogen-free deionized water. For measurements at pH 9, a buffered solution was made by adding 6 ml pH 9 buffer (Fisher Scientific Co. catalog number SB114-500) and 2 ml pH 10 buffer (Fisher Scientific Co. catalog number SB116-500) to 1 liter pyrogen-free deionized water. The electrical potential across the filter holder was measured during flow (it required about 30 seconds of flow for the potential to stabilize) and was corrected for cell polarization by subtracting from it the electrical potential measured when flow was stopped. During the period of flow the pH of the liquid was measured using a Cole-Parmer model J-5994-10 pH meter fitted with an in-line model J-5993-90 pH probe. The conductivity of the liquid was measured using a Cole-Parmer model J-1481-60 conductivity meter fitted with a model J-1481-66 conductivity flow cell. Then the polarity of the volt meter was reversed, and the effluent was flowed backwards through the filter holder using a differential pressure of 45 inches of water column. As in the first instance the electrical potential measured during flow was corrected for cell polarization by subtracting from it the electrical potential measured after flow was stopped. The average of the two corrected potentials was taken as the streaming potential.

The zeta potential of the medium was derived from the streaming potential using the following relationship (J. T. Davis et. al., *Interfacial Phenomena*, Academic Press, New York, 1963):

$$\text{Zeta Potential} = \frac{4\pi n}{DP} \cdot E_S \lambda$$

where n is the viscosity of the flowing solution, D is its dielectric constant, $\lambda$ is its conductivity, $E_S$ is the streaming potential and P is the pressure drop across the sample during the period of flow. In these tests the quantity $4 \pi n / DP$ was equal to 0.800.

EXAMPLES

Each of the examples was run using the following basic procedure to process and test a bag of donated blood. The blood collection set was constituted as shown in FIG. 3. Bag 11, into which anticoagulant had been placed, was used to collect one unit of about 450cc of blood from a human volunteer. Bag 11 along with its two satellite bags 18, 41 was then centrifuged for 5 minutes at 2280×gravity, causing the red cells to sediment into the lower parts of the collection bag and leave a transparent, yellowish layer of red cell-free plasma in the upper part of the collection bag. This bag was then transferred, with care not to disturb its contents, to a plasma extractor. With tube 20 clamped adjacent to bag 11 to prevent flow, tube 20 was cut and red cell barrier filter assembly 12 and/or leucocyte depletion filter assembly 13 were inserted at the position as shown in FIG. 3. With the plasma extractor applying sufficient force to the bag to generate a pressure of about 200 to 300 millimeters of mercury within the bag, the clamp on tube 20 was removed, allowing the supernatant liquid to flow through the filter assemblies 12 and/or 13 into bag 41 which had been placed on a weight scale. One of several skilled operators was instructed to signal when, in normal blood bank practice, flow would have been manually shut off. For examples 1 and 2, which were in accordance with an embodiment of the invention having a PRP leucocyte depletion filter assembly 13, tube 20 was at the signal promptly shut-off, the weight of PRP collected was recorded, and the contents of the bag analyzed, with results recorded in Table I.

For examples 3–8 and 9–10, the weight of the PRP bag 41 was recorded at the signal, i.e., the precise moment when flow would in normal blood bank practice have been shut off, while flow was allowed to continue until the red cell layer reached red cell barrier filter assembly 12, at which time flow automatically and abruptly stopped, and the weight of PRP collected was recorded. The results for examples 3–8 are shown in Table II, and for examples 9 and 10 in Table III.

In each of the ten examples, the resulting PRP was visually free of red cells, and weights of the PRP were converted to volume by dividing by the density of plasma (1.04 g/cc). The data on residual leucocyte content of the PC derived from the filtered PRP are reported in Tables II and III as multiples of $10^7$ (i.e., $\times 10^7$), which can be conveniently compared with a target criterion of fewer than about $1 \times 10^7$ leucocytes per unit, which is a level believed adequate to significantly reduce alloimmunization in patients receiving platelet transfusions.

The widely used melt blowing process for making fibrous plastic webs is a convenient, economical, and effective means for manufacturing fibrous webs with fiber diameter in the 1–4 μm range. It is characteristic of this process that the Quality of melt blown webs is optimal when the web weight is maintained in a preferred range of about 0.0005 to about 0.01 g/cm$^2$, and more preferably between about 0.0005 and about 0.007 g/cm$^2$. For this reason, the webs used to form the examples of this invention were, wherever necessary, formed by laying up two or more layers of web of weight about 0.006 g/cm$^2$, and then hot compressing these to form an integral filter element.

EXAMPLES 1–2

PRP leucocyte depletion filter assemblies were prepared in the manner described in the specification. The filter elements of these devices were preformed from 2.6 μm average diameter PBT fibers, which had been surface modified in the manner as described above and as taught in U.S. Pat. No. 4,880,548 using a mixture of hydroxyethyl methacrylate and methacrylic acid in a monomer ratio of 0.35:1 to obtain a CWST of 95 dynes/cm and a zeta potential of −11.4 millivolts. Filter element effective diameter was 4.74 cm, presenting a filter area of 17.6 cm$^2$, thickness was 0.15 cm, voids volume was 83% (density=0.23 g/cc), and fiber surface area was 0.69 M$^2$. The volume of PRP held up within the filter housing was 2.5 cc, representing a loss of PRP due to hold-up of about 1%. The results, obtained using the operating procedure described earlier in this section, are shown in Table I.

TABLE I

Leucocyte Depletion Efficiency of the First Variation

| Example Number | Volume of PRP passed, cc | Leucocyte content of PC after filtration (per unit)* | Leucocyte removal efficiency,** % |
|---|---|---|---|
| 1 | 237 | <.006 × 10$^7$ | >99.9% |
| 2 | 206 | <.006 × 10$^7$ | >99.9% |

*Total leucocyte count in the PC after centrifuging the filtered PRP to obtain the PC.
**Assumes that the leucocyte content of the PRP prior to filtration conformed to an average value of 5 × 10$^7$ per unit.

EXAMPLES 3–8

Red cell barrier filter assemblies were prepared in the manner described in the specification. The filter elements of these devices were preformed from 2.6 μm average diameter PBT fibers, which had been surface modified in the manner as described above and as taught in U.S. Pat. No. 4,880,548 using hydroxyethyl methacrylate and methacrylic acid in a monomer ratio of 0.35:1 to obtain a CWST of 95 dynes/cm and a zeta potential −11.4 millivolts. The filter element's effective diameter was 2.31 cm, presenting a filter area of 4.2 cm$^2$, thickness was 0.051 cm, voids volume was (density, 0.34 g/cc), and fiber surface area was m$^2$.

The volume of PRP held up within the filter housing was <0.4 cc, representing a loss of PRP due to hold-up of less than 0.2%. In each test, flow stopped abruptly as red cells reached the upstream surface of the filter element, and there was no visible evidence of red cells or hemoglobin downstream. The results obtained, using the operating procedure described earlier in this section for the second variation, are shown in Table II.

TABLE II

| 1 Example Number | 2 Estimate volume/PRP using normal blood bank practice, ml | 3 Volume of PRP obtained using the procedure of invention, ml | 4 Incremental volume, percent | 5 Leucocyte content after filtration (per unit) of PC × 10$^7$ |
|---|---|---|---|---|
| 3 | 175.2 | 178.8 | 2.0 | 1.0 |
| 4 | 212.9 | 218.8 | 2.7 | 1.7 |
| 5 | 221.1 | 225.7 | 2.0 | 0.5 |
| 6 | 185.9 | 191.4 | 2.9 | 0.2 |
| 7 | 257.2 | 263.2 | 2.3 | >0.1 |
| 8 | 196.6 | 200.7 | 2.1 | 0.1 |

*Total leucocyte count in the PC after centrifuging the filtered PRP to obtain PC.

EXAMPLES 9–10

Combined PRP leucocyte depletion/red cell barrier filter assemblies were prepared in the manner described in the specification i.e., the combination of an automatic shut-off valve and a high efficiency filter, both included in a single filter. The filter elements of these devices were preformed from 2.6 μm average diameter PBT fibers, which had been surface modified in the manner as described above and as taught in U.S. Pat. No. 4,880,548 using a mixture of hydroxyethyl methacrylate and methacrylic acid in a monomer ratio of 0.35:1 to obtain a CWST of 95 dynes/cm and a zeta potential of −11.4 millivolts at the pH of plasma (7.3). The filter element effective diameter was 2.31 cm presenting a filter area of 4.2 cm$^2$ thickness was 0.305 cm, density was 0.31 g/cc (voids volume=77.5%), and fiber surface area was 0.46 M$^2$. The volume of PRP held up within the filter housing was 1.3 cc, representing a loss of PRP due to hold up within the filter of about 0.5%. In each case, flow stopped abruptly as red cells reached the upstream surface of the filter element, and there was no visible evidence of red cells or hemoglobin downstream. The results obtained, using the operating procedure described earlier in this section are shown in Table III.

TABLE III

Incremental Volume and Leucocyte Depletion Efficiency of the Third Variation

| Example Number | Estimated volume/PRP using normal blood bank practice, ml | Volume of PRP obtained using the procedure of invention, ml | Incremental volume, % | Leucocyte content after filtration (per unit of PC* × $10^7$) | Leucocyte removal efficiency** |
|---|---|---|---|---|---|
| 9 | 251 | 256 | 2 | <.004 | >99.9% |
| 10 | 212 | 216 | 1.9 | .005 | >99.9% |

*Total leucocyte count in the PC after centrifuging the filterd PRP to obtain PC.
**Assumes that the leucocyte content of the PRP prior to filtration conformed to an average value of 5 × $10^7$ per unit.

EXAMPLE 11

The processing system used to perform this example is set up in a manner that generally corresponds to that shown above, with the difference in this example pertaining to the red cell barrier filter assembly.

The red cell barrier filter assembly is configured in a manner that generally corresponds to FIGS. 1 and 2. The housing, having a radially positioned inlet and outlet, includes four ribs 8 on the inlet side, and, on the outlet side, concentric channels 9a and eight radial channels 9b in fluid communication with the outlet. The porous medium of the red cell barrier filter assembly, positioned in the housing between the inlet and the outlet, includes three zones of differing density, with the lowest density at the upstream side of the medium, and increasing toward the highest density at the downstream side of the medium. The first (upstream) zone of the porous medium has a density of about 0.130 g/cc. The second (middle) zone of the porous medium has a density of about 0.236 g/cc, while the third (downstream) zone of the porous medium has a density of about 0.294 g/cc.

The zones of the porous medium are preformed from 2.6 micron average diameter PBT fibers, which have been surface modified in the manner as described above and as taught in U.S. Pat. No. 4,880,548, using a mixture of hydroxyethyl methacrylate and methacrylic acid in a monomer ratio of 0.35:1 to obtain a CWST of 95 dynes/cm and a zeta potential of −11.4 millivolts.

For each of the 20 tests summarized in this example, a human volunteer donates a unit of whole blood, which passes through the needle line to be collected in the collection bag (which already contains anticoagulant). After mixing the blood with the anticoagulant in the collection bag, air may be displaced into the needle line by stripping blood from the needle line into the blood bag without releasing the stripper. The blood bag may be oriented so that the remaining air bubble is just below the needle line, and then the stripper may be released, and the needle line tubing may be sealed, e.g., heat sealed.

Within approximately 8 hours after collection, the blood is processed as described in the previous examples. As the PRP is expressed from the collection bag, the red cell barrier assembly is held horizontally, with the outlet of the assembly facing up, for priming. Once the PRP enters the inlet of the assembly, the assembly may be laid down, if desired. PRP may be expressed from the blood collection bag until red cells reach the upstream surface of the porous medium, at which point the flow abruptly stops, signalling the completion of filtration. The tubing from the outlet side of the red cell barrier filter assembly may be clamped and heat sealed, and the PRP bag may then be removed for further processing.

The PRP may be processed according to normal blood bank procedures to create plasma and PC. Platelet counts may be taken and averaged for the 20 samples, and compared to the average platelet counts of 20 units of PC prepared by conventional methods (i.e., without the red cell barrier filter assembly) and obtained from a local blood bank. Using conventional methods, the average platelet count may be about 6–7 × $10^{10}$ platelets per bag, while using the method according the instant invention may yield a platelet count of about 9–9.5 × $10^{10}$ platelets per bag, reflecting an increased yield of over 20%.

While the invention has been described in some detail by way of illustration and example, it should be understood that the invention is susceptible to various modifications and alternative forms, and is not restricted to the specific embodiments set forth in the Examples. It should also be understood that these Examples are not intended to limit the invention but, on the contrary, the intention is to cover all modifications, equivalents, and alternatives falling within the spirit and scope of the invention.

What is claimed is:

1. A device for harvesting platelets from a platelet-containing solution comprising a porous medium which blocks red blood cells, but which permits platelets to pass therethrough, said porous medium having zones of different density.

2. The device of claim 1 wherein the porous medium is fibrous.

3. The device of claim 2 wherein the porous medium has a CWST greater than about 70 dynes/cm.

4. The device of claim 3 wherein the porous medium has a flow area of about 3 $cm^2$ to about 8 $cm^2$.

5. The device of claim 2 wherein the porous medium includes fibers modified by exposure to a monomer comprising a polymerizable group and a hydroxyl-containing group.

6. The device of claim 5 wherein the monomer is hydroxyethyl methacrylate.

7. The device of claim 6 wherein the fibers of the porous medium have been modified to present hydroxyl groups and carboxyl groups.

8. The device of claim 7 wherein the fibers of the porous medium have been modified with a mixture of monomers comprising hydroxyethyl methacrylate and methacrylic acid.

9. The device of claim 8 wherein the weight ratio of the methacrylic acid monomer to the hydroxyethyl methacrylate monomer in the modifying mixture is between about 0.01:1 and about 0.5:1.

10. The device of claim 9 wherein the ratio in the modifying mixture is about 0.05:1 to about 0.35:1.

11. The device of claim 10 wherein the porous medium comprises polybutylene terephthalate fibers.

12. The device of claim 10 wherein the flow area of the fibrous porous medium is about 3 to about 8 cm$^2$.

13. The device of claim 12 wherein the flow area is about 4 to about 6 cm$^2$.

14. The device of claim 10 wherein the zeta potential of the fibrous porous medium is about −3 to about −30 millivolts at a pH of 7.3.

15. The device of claim 10 including a hold-up volume less than about 1 cc.

16. The device of claim 1 wherein the porous medium comprises at least two zones of different density.

17. The device of claim 16 wherein each zone is of successively increasing density.

18. The device of claim 17 wherein an upstream zone includes a density range from about 0.1 g/cc to about 0.2 g/cc, an intermediate zone includes a density range from about 0.20 g/cc to about 0.25 g/cc, and a downstream zone includes a density range from about 0.23 g/cc to about 0.40 g/cc.

19. The device of claim 16 wherein an upstream zone includes a density range from about 0.18 g/cc to about 0.23 g/cc, and a downstream zone includes a density range from about 0.23 g/cc to about 0.40 g/cc.

20. The device of claim 16 wherein the porous medium has a negative zeta potential.

21. The device of claim 9 including a hold-up volume less than about 1 ml.

22. A system for the collection and processing of blood comprising:
a blood collection bag and at least one satellite bag connected thereto;
a porous medium interposed between the blood collection bag and a satellite bag, the porous medium comprising fibers having a CWST of greater than about 70 dynes/cm, at least two zones of different density between about 0.1 g/cc and about 0.4 g/cc, and said porous medium bars the passage of red blood cells therethrough, but permits the passage of platelets.

23. The system of claim 22 wherein the porous medium has a negative zeta potential.

24. A device for producing a platelet suspension comprising:
a porous medium that decreases red blood cell contamination by permitting the passage of platelets until the medium is blocked by red blood cells;
said medium having zones of different density, and a negative zeta potential.

25. The device of claim 24 wherein the porous medium comprises a fibrous medium having a CWST of greater than about 70 dynes/cm.

26. The device of claim 25 wherein the CWST is from about 90 dynes/cm to about 100 dynes/cm.

27. The device of claim 26 wherein the CWST is from about 93 dynes/cm to about 97 dynes/cm.

28. The device of claim 24 wherein the porous medium is preformed prior to assembly into a housing.

29. The device of claim 24 further comprising a housing including an inlet and an outlet and defining a fluid flow path between the inlet and the outlet, said porous medium disposed in the housing across the fluid flow path.

30. The device of claim 29 wherein the housing includes a radially positioned inlet and a radially positioned outlet.

31. The device of claim 30 wherein the housing includes at least one rib facing the upstream side of the porous medium, and at least one channel facing the downstream side of the porous medium.

32. The device of claim 31 wherein the housing includes concentric grooves and radial channels facing the downstream side of the porous medium.

33. The device of claim 29 further comprising a container downstream of the housing.

* * * * *